(12) United States Patent
Marshall

(10) Patent No.: US 12,302,517 B1
(45) Date of Patent: May 13, 2025

(54) FITNESS DEVICE ENCLOSURE

(71) Applicant: Sam Marshall, Georgetown, TX (US)

(72) Inventor: Sam Marshall, Georgetown, TX (US)

( * ) Notice: Subject to any disclaimer, the term of this patent is extended or adjusted under 35 U.S.C. 154(b) by 152 days.

(21) Appl. No.: 18/144,185

(22) Filed: May 6, 2023

(51) Int. Cl.
| *G06F 3/04817* | (2022.01) |
| *H05K 5/00* | (2006.01) |
| *H05K 5/02* | (2006.01) |
| *H05K 5/06* | (2006.01) |
| *G06F 3/04847* | (2022.01) |

(52) U.S. Cl.
CPC .......... *H05K 5/023* (2013.01); *H05K 5/0018* (2022.08); *H05K 5/0204* (2013.01); *H05K 5/0247* (2013.01); *H05K 5/06* (2013.01); *G06F 3/04817* (2013.01); *G06F 3/04847* (2013.01)

(58) Field of Classification Search
None
See application file for complete search history.

(56) References Cited

U.S. PATENT DOCUMENTS

| 2006/0286944 | A1* | 12/2006 | Songwe, Jr. | ........... B60K 35/00 |
| | | | | 455/99 |
| 2008/0312902 | A1* | 12/2008 | Dollinger | ................ G06F 40/58 |
| | | | | 704/4 |
| 2012/0099261 | A1* | 4/2012 | Reber | .................. G06F 1/1632 |
| | | | | 361/679.3 |
| 2021/0170764 | A1* | 6/2021 | Park | ........................ B41J 29/13 |

* cited by examiner

*Primary Examiner* — Tuan S Nguyen

(57) ABSTRACT

An electronics enclosure for a portable physical fitness device includes features that function as ambidextrous positive grip handles, impact absorption, cable management, and reduction in accidental contact of a touch display. The enclosure also includes an optional removable VESA foot/grip/handle.

7 Claims, 3 Drawing Sheets

FITNESS DEVICE ENCLOSURE

TECHNICAL FIELD OF THE INVENTION

The present invention relates to electronics enclosures, and more specifically to portable physical fitness devices.

CROSS REFERENCE

Co-pending design application U.S. 29/891,506 FITNESS DEVICE ENCLOSURE.

BACKGROUND OF THE INVENTION

Electronics enclosures are available in a myriad of shapes and sizes. Portable/hand-held fitness devices are subject to frequent rough handling and droppage. Fitness devices are especially prone, as the user is generally not focused on care of the device while in use. One such device is described in U.S. Pat. No. 9,526,892B2. Also, a user may be in a very fatigued state, with weak or misjudged grip strength or poor coordination. Impact shock can result in significant internal damage, especially of heavy components, such as: transformers and batteries. Silicone shells or padded cases often provide impact resistance. Unfortunately, in a multi-user medical environment, silicone shells are time consuming to remove clean.

Devices such as electrical muscle stimulators generally have one, two, four, or more cables attached to skin electrodes. These cables can easily become tangled, leading to: delays in use to untangle cables, user frustration, or pulling the device off of the surface it is resting on.

Handling of a device weighing a kilogram or more easily results in accidental contact with a touch display, potentially causing unintended operation.

User input numeric settings are made with potentiometers, multi-turn digital click wheels, or up/down buttons. Channels may be linked, to apply the same user input to multiple channels, as to produce an identical output.

SUMMARY OF THE INVENTION

In accordance with the present invention, an electronics enclosure for a portable physical fitness device is provided which substantially eliminates or reduces disadvantages and problems associated with previous enclosures. In a particular embodiment, the present invention satisfies a need for protection from impact due to droppage, and a reduction of the rate of occurrence of droppage. Co-pending design application U.S. 29/891,503 FITNESS DEVICE ENCLOSURE is incorporated by reference.

According to one embodiment of the present invention, an enclosure includes features that multifunction as ambidextrous positive grip handles, impact absorption, cable management, and for reduction in accidental contact of a touch display.

In accordance with another embodiment of the present invention, the enclosure also includes an optional removable VESA portion which functions as a foot, ambidextrous grip, and handle.

In accordance with another embodiment of the present invention, numeric inputs may be made with a touch screen velocity slider, and may simultaneously adjust multiple values.

Various embodiments of the present invention provide numerous technical advantages. For handheld or portable devices weighing a kilogram or more and containing a large display, droppage may be frequent. Positive grips have the advantage of not relying on friction, which may be reduced by sweat or fatigue. When dropped, serpentine bends reduce the force of impact. Finger size serpentine bends have the advantages of providing positive grip, cable management, and reduction of unintentional display contact. The velocity slider and multi value input reduce interaction with the device, and associated risk of droppage.

Other technical advantages of the present invention will be readily apparent to one skilled in the art from the following figures, descriptions, and claims.

DETAILED DESCRIPTION OF THE DRAWINGS

Figure 1A:
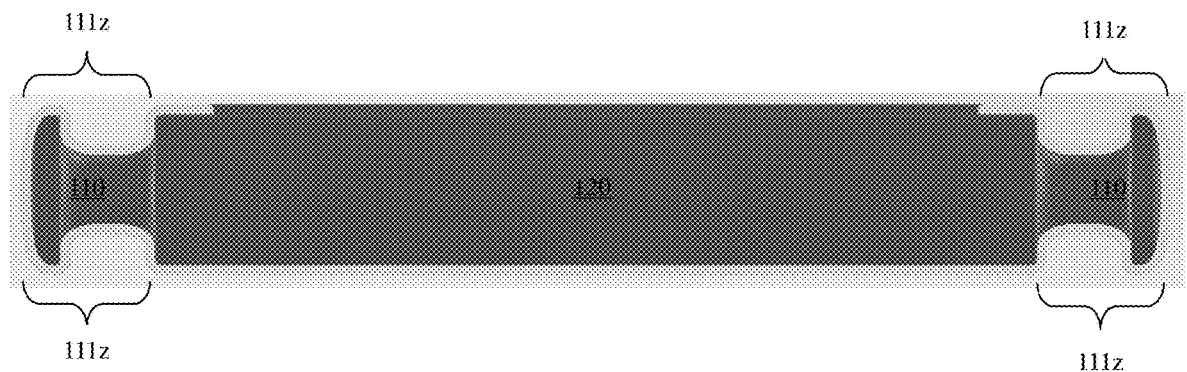
FIG. 1A illustrates a vertical cross section of a fitness device enclosure.
Figure 1B:
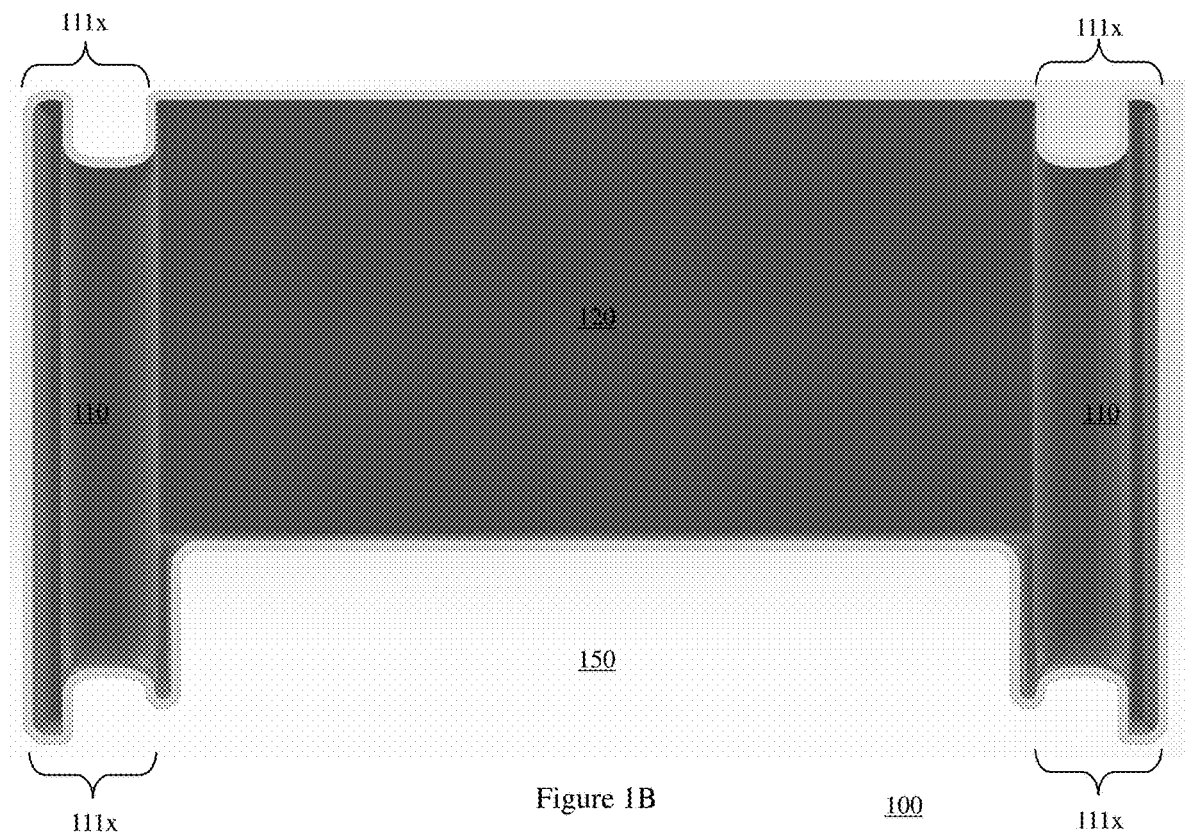
FIG. 1B illustrates a horizontal cross section of a fitness device enclosure.
Figure 1C:
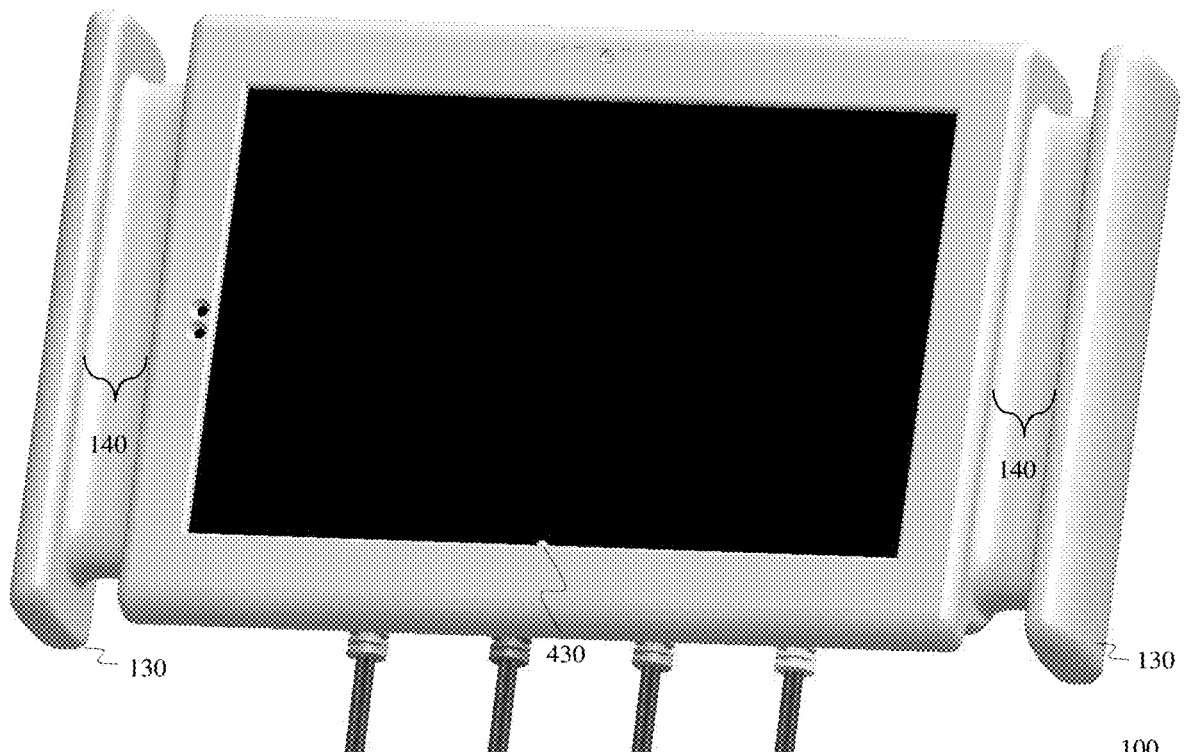
FIG. 1C illustrates a perspective view of a fitness device enclosure.

FIG. 1A illustrates a vertical cross section, FIG. 1B illustrates a horizontal cross section, and FIG. 1C illustrates a perspective view of a portable fitness device enclosure 100.

Enclosure 100 includes an electronics area 120 and impact absorbing areas 110. Enclosure 100 may be repetitively dropped during normal use. The device may weigh over 1 kilogram, over 2 kilograms, or more. It may contain heavy electronic components and devices, such as a power supply and transformers, which are more likely to sustain damage during impact from a drop. A need has arisen to minimize likelihood and severity of damage.

Impact absorbing areas 110 include multiple serpentines 111z and 111x in different planes, which flex during impact to reduce high transient forces. Serpentines isolate each corner of enclosure 100 from the electronics area 120. Serpentines 111z and 111x may be left/right bilaterally symmetric, and top/bottom bilaterally symmetric. Serpentines 111z and 111x include multiple bends. Bends may be: off odd number, asymmetric, with different radii of curvature, or do not need to form regular symmetric repeating S bends.

Drops on the flat faces will not engage serpentines 111z and 111x. However, perfectly flat drops are statistically unlikely, and electronic components may be less damaged by tensile shocks than shear shocks. In an alternate embodiment, the corners of enclosure 100 are extended beyond the faces (dog boned), such that a flat face drop in the Y direction will flex serpentines 111z and 111x.

Some of the serpentine bends may form a finger size groove 140 and handle 130, providing a positive grip, and allowing manipulation with sweaty or fatigued fingers. Excess length of user cables may be wrapped in groove 140, improving cable management. A recessed connector area 150 limits drop force from being directly applied to connectors.

Enclosure 100 may be sealed against water ingress, and the volume/mass ratio may provide positive buoyancy in water. If dropped in water, this prevents the device from sinking and being subjected to increasing water pressure as would a device that sinks.

Enclosure 100 may include a VESA mount. This enables a variety of interchangeable secure mounting options.

Portable is broadly used to also include handheld, and body worn wearable uses. Fitness device is broadly used to also include medical devices. The device may contain a 10" or greater touch screen.

Enclosure 100 may be formed by injection molding. The device may be an electrical muscle stimulator, TENS, NEMS device.

Figure 2A:
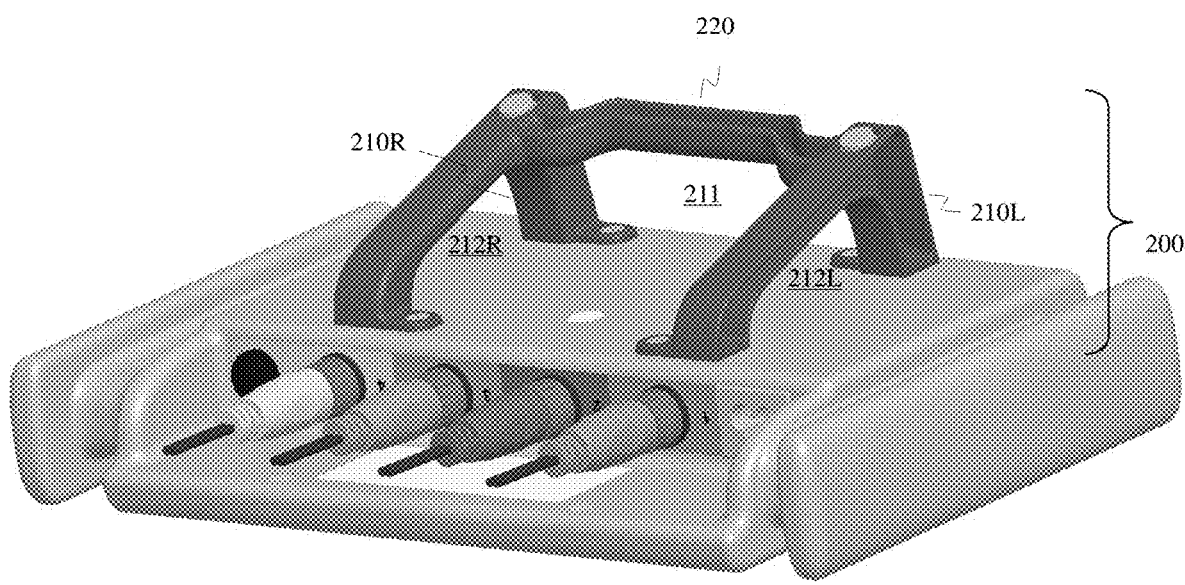
FIG. 2A illustrates a VESA foot for a fitness device enclosure.

FIG. 2A illustrates a multifunction VESA foot 200 coupled to portable fitness device enclosure 100. Multifunction foot 200 includes a handle 220.

Multifunction foot 200 may be held in the orientation of a platter, with the left hand, post 210L between the thumb through orifice 212L and fingers through orifice 211. Or, with the right hand, post 210R between the thumb through orifice 212R and fingers through orifice 211. Both grips are bilaterally symmetric, and are positive grips that cannot easily slip free even with slippery or fatigued hands, or an open grip.

Figure 2B:
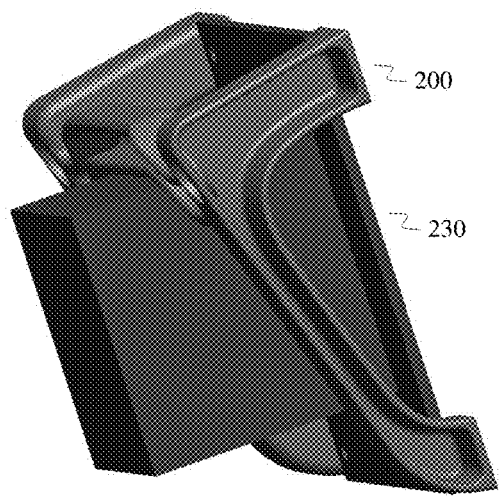
FIG. 2B illustrates a stacked VESA foot for a fitness device enclosure.

FIG. 2B illustrates a stacked VESA foot for a fitness device enclosure. Multifunction foot 200 may be of an open design, enabling stacking a second VESA device 230 in front of, or between foot 200 and enclosure 100. Only a single set of 4 screws is required. The second VESA device 230 may include a chest harness, or a VESA monitor arm with a quick connect. Foot 200 or second VESA device 230 may also provide attachment for a shoulder strap.

Figure 3:
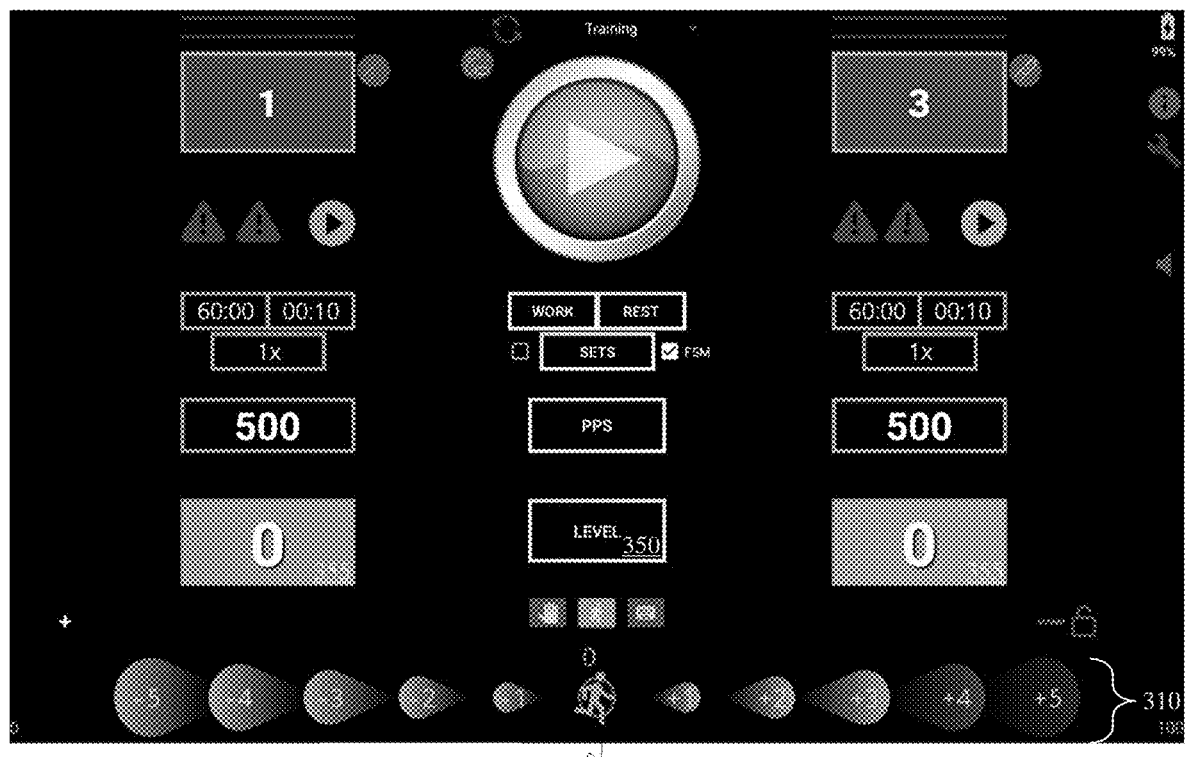
FIG. 3 illustrates a user interface layout for a fitness device.

FIG. 3 illustrates a user interface layout for a fitness device 300. Velocity slider 310 may input numeric values on a touch screen. An icon 320 is normally at a zero-velocity position. Sliding icon away from the zero velocity increments or decrements the user input value at a constant velocity proportional to the distance from the zero position. Releasing icon 320 returns icon 320 to the zero-velocity position. For well-known sliders, the value varies directly with position, not velocity. Preferably velocity slider 310 is located at the edge of the touch screen, such that the bezel provides a tactile guide, removing the need for a user to look at the screen to change values. The bezel may also include a tactile zero position 330. Preferably slider 310 may not extend to the corners of the display, such that unintentional contact that slides to a corner will produce no change in value. A variable intensity haptic feedback may also indicate velocity of change. Adjustment rates which may cause hazard may include a warning color. An advantage is both a high-resolution input and a large adjustment range. Additional advantages include easier user input, and fewer errors, reducing the incidence of droppage.

If certain fields are desired to be shared between channels and other fields desired to not be shared, a row may be linked, simultaneously changing only that field across all channels. It is well known, if multiple channels are desired to operate with all of the same parameters, channels may be linked or bonded. For instance, row link button 350 may link a single user input across all similar fields 355.

A play all button to enable all channels may be centrally located, and a lock screen excluding stop buttons may reduce the incidence of accidental fat fingering inputs. A pause button and progress bar may further increase usability. Channel identification colors may be paired in color space.

What is claimed is:

1. An electronics enclosure for a portable fitness device, said enclosure comprising:
   multiple serpentine bends in two orthogonal planes, forming a shock absorbing section; and
   an electronics section;
   wherein two of said serpentine bends are bilaterally symmetric;
   wherein the corners of said shock absorbing section extend beyond multiple faces of said electronics section;
   wherein said serpentine bends form a finger size groove in handle, providing a positive gripping surface;
   wherein a recessed connector area such that the mating connector is predominantly within a bounding box of said enclosure;
   wherein said enclosure includes a VESA mount;
   wherein a VESA foot is coupled to said VESA mount;
   wherein said foot includes a handle;
   wherein said foot includes two posts, operable to be positively retained between fingers, with an open hand grip; and
   wherein the said posts are bilaterally symmetric.

2. The enclosure of claim 1, wherein said serpentine bends form a hollow spindle, providing a user cable wrapping volume.

3. The enclosure of claim 1, wherein said enclosure is sealed against water intrusion and has positive buoyancy.

4. The enclosure of claim 1, wherein said serpentine bends are selected such that a device weighing over 1 kilogram may survive a drop.

5. The enclosure of claim 1, wherein said foot is operable to stack with a second VESA device, where a single set of screws couples both said VESA foot and said second VESA device to said VESA mount.

6. The enclosure of claim 5, wherein said second VESA device includes a chest harness.

7. The enclosure of claim 5, wherein said second VESA device includes a quick connect coupled to a VESA monitor arm.

* * * * *